United States Patent [19]
Yannopoulos et al.

[11] Patent Number: 5,932,176
[45] Date of Patent: Aug. 3, 1999

[54] HALOGEN GAS DETECTOR

[75] Inventors: Lymperios N. Yannopoulos, Pittsburgh; Robert A. Peters, Harmony; John E. Tozier, Wexford, all of Pa.

[73] Assignee: Bacharach, Inc., Pittsburgh, Pa.

[21] Appl. No.: 09/110,705

[22] Filed: Jul. 7, 1998

[51] Int. Cl.⁶ .................................................. G01N 27/12
[52] U.S. Cl. .......................................... 422/98; 73/31.05
[58] Field of Search .............................. 422/98; 73/31.05

[56] References Cited

U.S. PATENT DOCUMENTS

| | | | |
|---|---|---|---|
| 3,751,968 | 8/1973 | Loh et al. | 73/23 |
| 3,979,625 | 9/1976 | Roberts | 73/31.05 |
| 3,991,360 | 11/1976 | Orth et al. | 324/33 |
| 4,045,729 | 8/1977 | Loh | 324/71 SN |
| 4,151,641 | 5/1979 | Mitoff | 29/611 |
| 4,161,513 | 7/1979 | Forberg et al. | 423/598 |
| 4,196,427 | 4/1980 | Rudberg | 436/124 |
| 4,296,399 | 10/1981 | John | 29/605 |
| 4,447,397 | 5/1984 | Anouchi et al. | 73/31.05 |
| 4,668,477 | 5/1987 | Nishio et al. | 422/98 |
| 4,916,935 | 4/1990 | Novack et al. | 73/27 R |
| 5,104,513 | 4/1992 | Lee et al. | 204/425 |
| 5,224,972 | 7/1993 | Frye et al. | 55/18 |
| 5,528,225 | 6/1996 | Sakai et al. | 422/98 |

FOREIGN PATENT DOCUMENTS

| | | |
|---|---|---|
| 4339737 C1 | 1/1995 | Germany . |
| 2166247 | 4/1986 | United Kingdom . |

OTHER PUBLICATIONS

Holzinger, M.; Maier, J.; and Sitte, W. "Fast CO2–Selective Potentiometric Sensor with Open Reference Electrode." Solid State Ionics 86–88, 1055–1062, Jun. 1996.

*Primary Examiner*—Jill Warden
*Assistant Examiner*—Kevin P. Cannell
*Attorney, Agent, or Firm*—Webb Ziesenheim Logsdon Orkin & Hanson, P.C.

[57] ABSTRACT

A halogen gas detector comprises a coil comprising an oxidation-resistant metal wire with a nonreactive oxide coating wound into a double helix defining a cylindrical space, a conductive metal pin positioned within the cylindrical space making no contact with the coil, finely divided sintered in place sodium titanate filling the space between the coil and the pin.

5 Claims, 3 Drawing Sheets

HALOGEN GAS DETECTOR

BACKGROUND OF THE INVENTION

Gas detectors for sensing halogenated gases and other gases by the effects of such gases on the electrical properties of certain materials are known. Gas detectors of this type include those described in the following patents: Loh et al. U.S. Pat. No. 3,751,968 entitled "Solid State Sensor", Loh U.S. Pat. No. 4,045,729 entitled "Gas Detector" and Lee et al. U.S. Pat. No. 5,104,513 entitled "Gas Sensor". Common to all of these patents are a helical coil and pin positioned within the coil spaced from each other by a material that changes electrical resistance, as measured by change in current or voltage, when in the presence of the gas to be detected.

The industry is constantly striving for improvements in this type of detector, particularly in sensitivity to refrigerant vapors, life, power consumption and cost. It is very important that the detector must detect refrigerant vapors of the R-134a, R-12 and R-22 types.

It is an advantage, according to this invention, to provide a thermally efficient gas detector that consumes less power than prior gas detectors, thus extending battery life.

It is another advantage, according to this invention, to provide a gas detector that operates at a higher voltage and thus a lower current draw on the battery.

It is a further advantage, according to this invention, to provide a gas detector that is substantially silica free.

It is a yet further advantage, according to this invention, to provide a gas detector that is easy to manufacture.

SUMMARY OF THE INVENTION

Briefly, according to this invention, there is provided a halogen gas detector comprising a collector comprising an oxidation-resistant noble metal wire with a nonreactive electrically insulating oxide coating wound into a helical coil defining a cylindrical space and a conductive noble metal pin positioned within the cylindrical space. Finely divided sintered in place sodium titanate, optionally, mixed with titanium oxide or other inert material, fills the space between the coil and the pin. A circuit with leads connected to a battery is provided for causing an electrical current to flow in the coil to raise the temperature thereof. Another circuit including leads is provided for applying a voltage between the coil and pin and sensing a change in current between the coil and pin indicative of the presence of halogen gas.

According to a preferred embodiment, the coil is wound with two or more layers. In one embodiment, the coil is formed from 1 mil wire wrapped into a double layer coil of about 20 turns, 10 turns wrapped over the other 10 turns such that the inner diameter of the coil is at least 11 mils. According to a preferred embodiment, the coil wire and pin are comprised of a nonoxidizing noble metal. In one embodiment, the coil wire and pin are comprised of platinum or a platinum alloy. According to a preferred embodiment, the noble metal wire is precoated with a nonsilicious insulating oxide coating to prevent shorting along the coil.

BRIEF DESCRIPTION OF THE DRAWINGS

Further features and other objects and advantages will become clear from the following detailed description made with reference to the drawings in which.

DESCRIPTION OF THE DETAILED EMBODIMENTS

Figure 1:
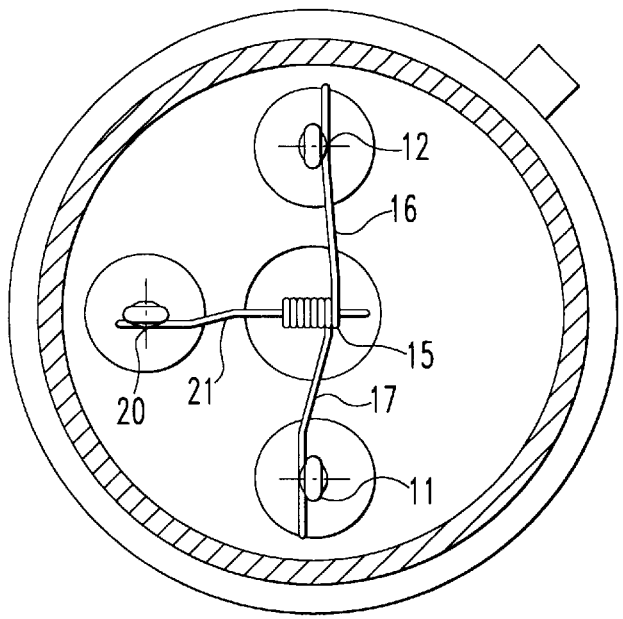
FIG. 1 is a broken away top view of a gas sensor, according to this invention.
Figure 2:
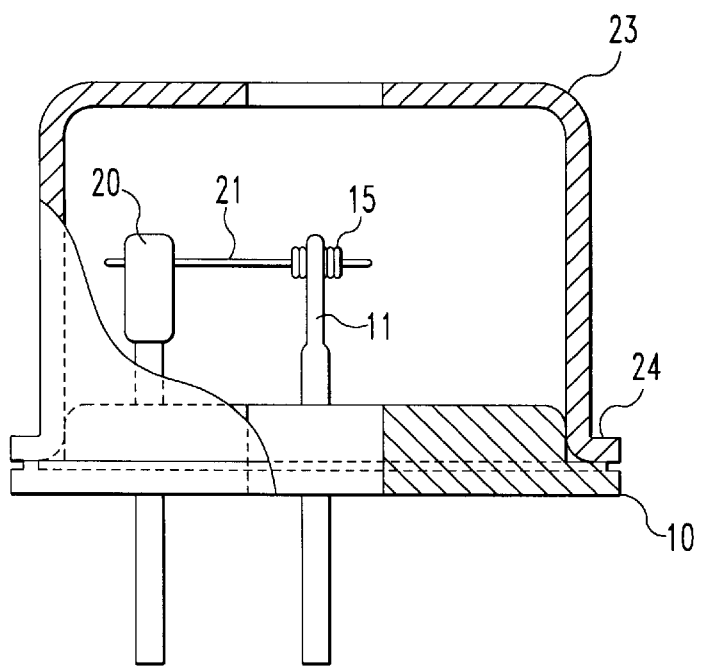
FIG. 2 is a broken away side view of a gas sensor, according to this invention.
Figure 3A:
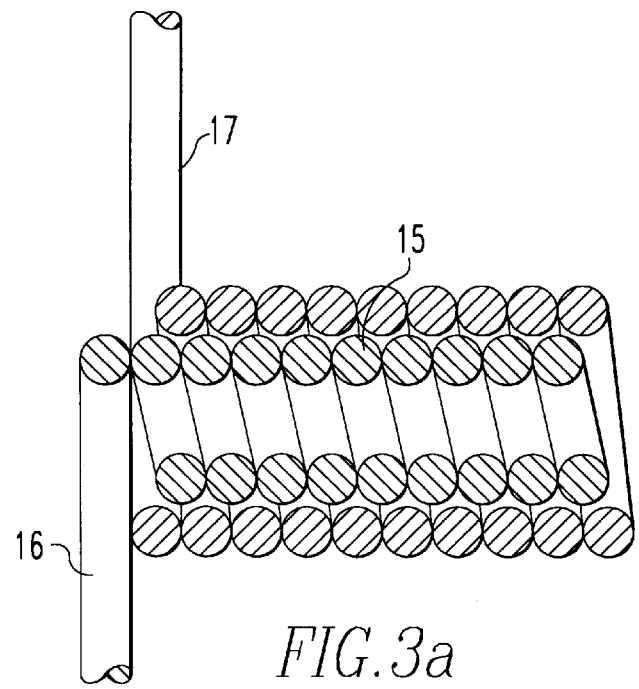
FIGS. 3a and 3b are a detailed section view and end view, respectively, of a double layer coil used in gas sensors, according to this invention.
Figure 3B:
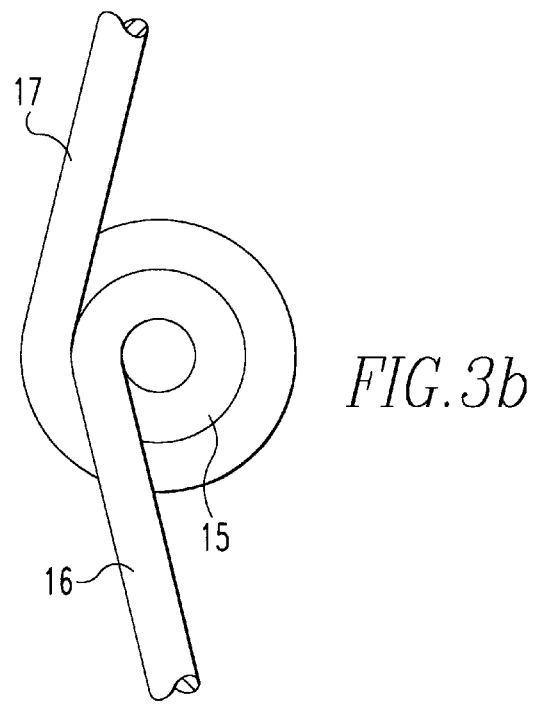

Referring now to FIGS. 1, 2 and 3a and 3b, a halogen gas sensor is comprised of an electrically insulating base 10 with three electrically conductive posts secured in the base. Two of the posts 11, 12 support the ends of leads 16, 17 of coil 15 in the form of a double layer coil (one layer wound over the other layer as shown in FIGS. 3a and 3b). The coil is formed from alumina precoated 1 mil wire wound into a double layer coil 20 turns, 10 turns wrapped over the other 10 turns such that the inner diameter of the precoated wire coil is at least 11 mils. The coil wire is comprised of a noble or oxidation-resistant metal, such as platinum (the most common), ruthenium, rhodium, palladium, osmium, and iridium and alloys thereof. The diameter of the wire and the length of the wire (coil and leads) are selected to provide a resistance in excess of about 10 ohms. The coil wire is precoated with a nonsilicious metal oxide, such as alumina, titania, thoria or stabilized zirconia and mixtures thereof. The refractory oxide, preferably alumina, is in the form of a fine powder that is held to the wire by binders and sintered. The coating is from 1 to 3 mils thick. With the coating, the wire is still flexible enough to form into the double layer coil. Post 20 is secured in the base and supports pin 21 which extends into the cylindrical space defined by the interior of the coil 15. The pin is comprised of a noble or oxidation-resistant metal and may be precoated in the same manner as the wire used to form the coil. A partial cover 23 is secured to the periphery 24 of the base 10.

Slurries of the finely divided sodium titanate in a suitable vehicle are applied on the alumina precoated wire coil and pin and dried until a coating 22 fills the core of the coil around the pin and to the extent the individual coil turns are no longer distinguishable. The sodium titanate can be mixed with a filler selected from nonsilicious oxides that do not interfere with the changing electrical properties of the sodium titanate in the presence of halogen gases, most preferably, titania. The amount of filler is not critical so long as it does not adversely affect the changing electrical properties. Preferably, the sodium titanate comprises at least 80% by weight of the solids content of the slurry. Typically, the sodium titanate is a soft powder, say, all passing 325 mesh. The precoating on the wire is porous and the sodium titanate appears to penetrate the alumina precoating. The coated coil and pin are then heated to presinter the coating. The presintering takes place by passing a current through the coil to obtain a presintering temperature and the temperature is held for a very short time, say, one minute. The active coating does not form a vitreous or glass mass but the finely divided sodium titanate particles are bonded together where touching. Immediately after this presintering, further sintering and aging take place at the operating coil temperatures with the applied operating bias between the coil and pin and holding for a period of time, say 3 to 12 hours.

In the finished titanate coated pin/coil configuration, the alkali metal ions of the titanate coating are the receptors of negative ions (in this case, the halide ions of the halogenated vapors). With heating under the applied bias, an outer layer depleted of ions develops along the boundaries of the titanate coating and the electrodes (pin and coil). Exposure of this ion depleted layer to reactive gases like halogen causes ions to flow across the depletion zone and increase the conductivity of the device.

Figure 4:
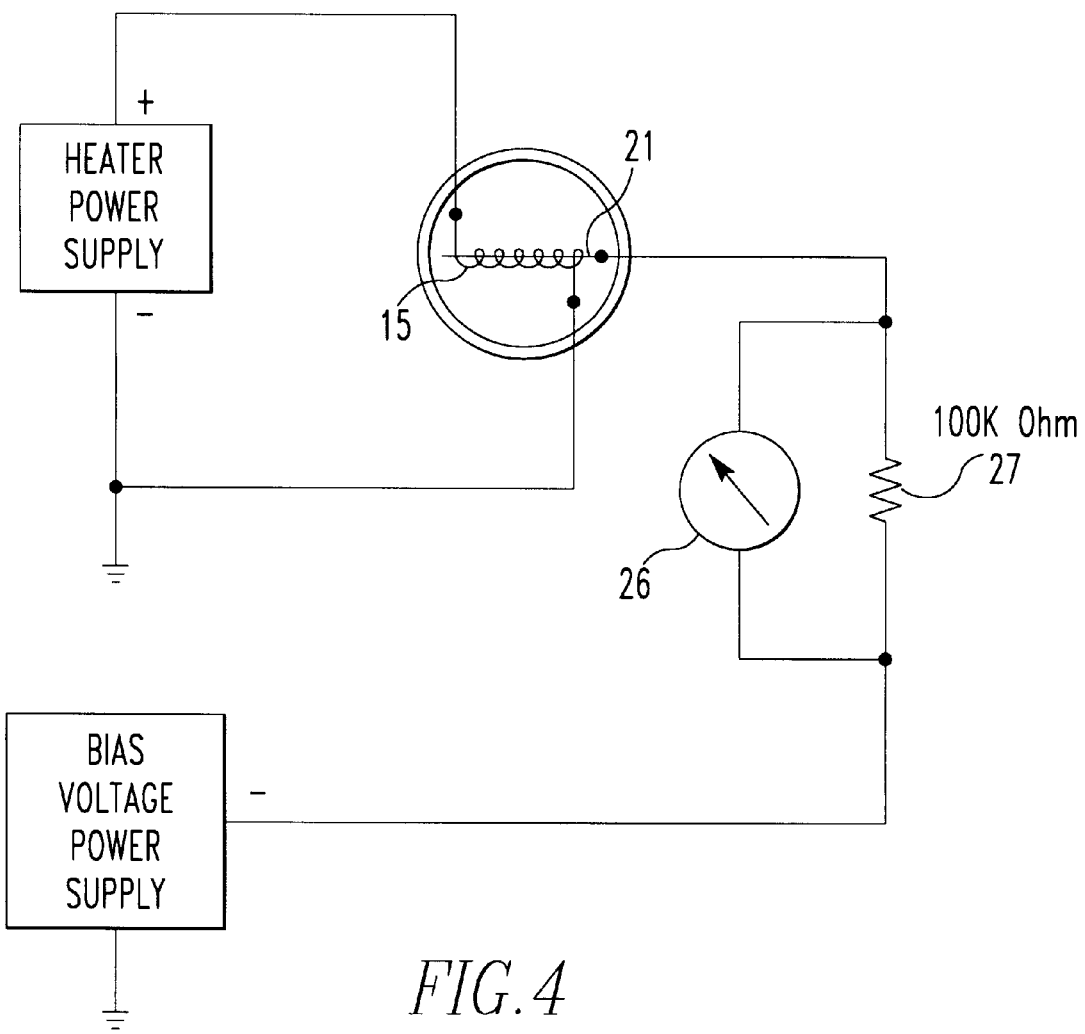
FIG. 4 is an electrical schematic for explaining the operation of this invention.

The sensor is operated according to the schematic of FIG. 4. The applied bias, while not critical for the interposed titanate coating, is typically arranged to make the pin negative with respect to the coil. The current passing between the coil and pin measured by a voltmeter 26 in parallel with a resistance 27 is indicative of the presence or not of halogen-containing gases. The sensor, according to this invention, has good sensitivity to refrigerant vapors (R-134a, R-12 and R-22) with a low noise-to-signal ratio. The sensitivity is still acceptable after 100 hours of continuous use. This is about one year in intermittent field service. The low noise-to-signal ratio is believed to be due to the particular coating material and the compactness of the applied coating. During operation, the power consumption is on the order of 600 to 650 mW at operating voltages of about 4.1. This results in a very low current drain. By comparison, one popular prior art sensor consumes about 800 mW at voltages of about 1.2 and another with a heavy coil heater consumes about 6 watts.

Having thus defined our invention in the detail and particularity required by the Patent Laws, what is desired protected by Letters Patent is set forth in the following claims.

We claim:

1. A halogen gas detector comprising:
   a) a coil comprising an oxidation-resistant metal wire with a nonreactive oxide coating wound into a helix defining a cylindrical space;
   b) a conductive metal pin positioned within the cylindrical space making no electrical with the coil;
   c) finely divided sintered in place sodium titanate filling the space between the coil and the pin;
   d) means for causing an electrical current to flow in the coil to raise the temperature thereof;
   e) means for applying a voltage between the coil and pin; and
   f) means to sense change in electrical resistance between the coil and pin indicative of the presence of halogen gas.

2. The halogen gas detector according to claim 1, wherein the wire is wound into a multiple layer coil.

3. The halogen gas detector according to claim 1, wherein the wire is wound into a double layer coil.

4. The halogen gas detector according to claim 2, wherein the diameter of the coil wire and the length thereof are selected to provide at least 10 ohms resistance.

5. The halogen gas detector according to claim 1, wherein the finely divided sodium titanate is mixed with a nonsilicious filler material.

* * * * *

UNITED STATES PATENT AND TRADEMARK OFFICE
CERTIFICATE OF CORRECTION

PATENT NO. : 5,932,176
DATED : August 3, 1999
INVENTOR(S) : Lymperios N. Yannopoulos et al.

It is certified that error appears in the above-identified patent and that said Letters Patent is hereby corrected as shown below:

Claim 1 Column 4 Line 7 after "electrical" insert --contact--.

Signed and Sealed this

Twenty-fifth Day of January, 2000

Attest:

Attesting Officer

Acting Commissioner of Patents and Trademarks